United States Patent
Horsman et al.

[11] Patent Number: 6,019,897
[45] Date of Patent: Feb. 1, 2000

[54] SYSTEM FOR SIMULTANEOUSLY PUMPING SOLVENT FOR A PLURALITY OF CHROMATOGRAPHY COLUMNS

[75] Inventors: Jeffrey A. Horsman; Peter J. Leavesley, both of Charlottesville; Peter C. Rahn, Palmyra, all of Va.; Thomas R. Schumacher, Marshall, Wis.; Peter C. Van Davelaar, Maidens, Va.

[73] Assignee: Dyax Corporation, Cambridge, Mass.

[21] Appl. No.: 09/137,035

[22] Filed: Aug. 20, 1998

[51] Int. Cl.⁷ .................................................... B01D 15/08
[52] U.S. Cl. .................... 210/198.2; 210/656; 210/101
[58] Field of Search ................... 210/656, 659, 210/101, 198.2, 416.1; 95/82; 96/102

[56] References Cited

U.S. PATENT DOCUMENTS

| | | | |
|---|---|---|---|
| 3,923,460 | 12/1975 | Parrott .................................. | 210/198.2 |
| 4,093,550 | 6/1978 | Stahl et al. .............................. | 210/198 |
| 4,250,035 | 2/1981 | McDonald et al. ................... | 210/198.2 |
| 4,403,503 | 9/1983 | Banerjee ............................... | 210/198.2 |
| 4,483,374 | 11/1984 | Siemion ................................... | 141/9 |
| 4,565,632 | 1/1986 | Hatch et al. ........................... | 210/656 |
| 4,719,011 | 1/1988 | Shalon et al. ......................... | 210/198.2 |
| 4,769,141 | 9/1988 | Couillard .............................. | 210/198.2 |
| 4,876,005 | 10/1989 | America ................................ | 210/198.2 |
| 4,994,180 | 2/1991 | Sims et al. ............................. | 210/198.2 |
| 5,238,556 | 8/1993 | Shirkham .............................. | 210/198.2 |
| 5,324,427 | 6/1994 | Traveset-Masanes et al. ...... | 210/198.2 |
| 5,496,473 | 3/1996 | Chow .................................... | 210/198.2 |
| 5,580,523 | 12/1996 | Bard ..................................... | 210/198.2 |
| 5,601,708 | 2/1997 | Leavesley ............................. | 210/198.2 |
| 5,670,054 | 9/1997 | Kibbey ................................. | 210/198.2 |
| 5,766,460 | 6/1998 | Bergstrom ............................ | 210/198.2 |
| 5,766,481 | 6/1998 | Zambias ................................ | 210/659 |

OTHER PUBLICATIONS

Biotage brochure, Parallex HPLC, "Parallel Purification for Combinatorial Chemistry" 5 pages undated.

*Primary Examiner*—Ernest G. Therkorn
*Attorney, Agent, or Firm*—Fish & Richardson P.C.

[57] ABSTRACT

Apparatus for simultaneously supplying solvent to a plurality of chromatography columns using a plurality of pumps. Each pump has a chamber with a movable solvent piston therein and inflow and outflow valves. The outflow valve of each pump is connected to a respective chromatography column. The solvent pistons are simultaneously moved in one direction to pull solvent into the respective chambers until all pistons have achieved an adjustable stop position corresponding to a desired delivery volume. The solvent pistons are then simultaneously moved in the opposite direction to deliver solvent to the respective columns until all pistons have delivered the desired delivery volumes. The solvent pistons are driven by a common pneumatic or hydraulic system.

22 Claims, 2 Drawing Sheets

SYSTEM FOR SIMULTANEOUSLY PUMPING SOLVENT FOR A PLURALITY OF CHROMATOGRAPHY COLUMNS

BACKGROUND OF THE INVENTION

The invention relates to supplying solvent for a plurality of chromatography columns.

Liquid chromatography is a technique for separating the individual compounds that exist in a subject sample. In employing the technique, the subject sample is carried in a liquid, called a mobile phase. The mobile phase carrying the subject sample is caused to migrate through a media, called a stationary phase. Different compounds will have differing rates of migration through the media, which effects the separation of the components in the subject sample. Liquid chromatography is commonly performed with reusable or disposable columns, both of which are usually cylindrical, in which the media bed is bounded axially by porous plates, or by plates containing defined flowpaths, through which the mobile phase will flow. (See U.S. Pat. No. 5,601,708 to Leavesley, and U.S. Pat. No. 4,250,035 to McDonald et al.)

Traditional chromatography involves a batch process where one sample is injected into one column and one separation is achieved. Many efforts to provide improvements in efficiency have focussed on reducing the time required to run a separation in a single column.

There have been attempts to use a single pump to simultaneously provide solvent (i.e., the mobile phase) to multiple columns operating simultaneously; however this can result in an unequal distribution of flow, owing to different flow resistances in the respective columns.

One commercially available system, the Parallex HPLC available from the Biotage a division of Dyax Corporation, employs a common electrical motor to simultaneously drive pistons in four pumps supplying solvent to four respective chromatography columns connected in parallel.

SUMMARY OF THE INVENTION

In one aspect, the invention features, in general simultaneously supplying solvent to a plurality of chromatography columns using a plurality of pumps. Each pump has a chamber with a movable solvent piston therein and inflow and outflow valves. The outflow valve of each pump is connected to a respective chromatography column. The solvent pistons are simultaneously moved in one direction to pull solvent into the respective chambers until all pistons have achieved an adjustable stop position corresponding to a desired delivery volume. The solvent pistons are then simultaneously moved in the opposite direction to deliver solvent to the respective columns until all pistons have delivered the desired delivery volumes.

In another aspect the invention features, in general, using a plurality of pumps to simultaneously supply solvent to respective chromatography columns by simultaneously moving solvent pistons of the pumps first in one direction to stop positions and then in the opposite direction to deliver solvent. The pistons are moved in both directions by a common fluid pressure (e.g., pneumatic or hydraulic) delivery system.

In another aspect the invention features, in general, using a plurality of pumps to simultaneously supply solvent to respective chromatography columns and employing a fraction collection system to collect samples from the columns. The fraction collection system is advanced by a controller between pump strokes, and a pump cessation sensor senses that solvent pistons have ceased movement and provides a signal to the controller.

Embodiments of the invention may include one or more of the following features. Each pump includes a cylinder connected to the fluid pressure delivery system, and pressurized fluid is simultaneously delivered to the cylinders to move the solvent pistons. Each cylinder has first and second ports, and pressurized fluid is supplied to a first port to move the solvent piston in one direction, and pressurized fluid is supplied to the second port to move the solvent piston in the opposite direction. A controller is used to control valves permitting delivery of pressurized fluid to the first ports or the second ports. The solvent pistons stop moving in one direction when members operatively connected to the solvent pistons contact respective stop members. At least one solvent piston is moved to a different stop position and has a different desired delivery volume than another solvent piston. The piston drivers have adjustable stop positions; they have gross stop adjustment mechanisms and fine adjustment mechanisms for the stop positions. The pumps are arranged in rows, and rows of pumps are arranged in an array. Each row has a common stop position provided by a common stop mechanism.

Embodiments of the invention may include one or more of the following advantages. The system provides for very high throughput of solvent through chromatography columns. The system can be used to purify or analyze one sample using many different types of media or different solvent systems to evaluate the performance, selectivity, and differences. The system can deliver uniform volumes of solvent to multiple columns having different media and different flow resistances. If there is an obstruction preventing flow into one chromatography column, the other columns will continue to receive the flow of solvent while the obstructed column will not receive further flow or be subjected to increased pressure. The individual pumps can be adjusted to calibrate the delivered volume, and the stroke volumes can be set for a row of pumps in an array at one time. Guaranteed volumes are delivered to each column with each stroke. The actuating pressure in the air system can be set to limit the outlet pressure for the solvent.

Other advantages and features of the invention will be apparent from the following description of the preferred embodiment thereof and from the claims.

DESCRIPTION OF THE PREFERRED EMBODIMENT

Figure 1:
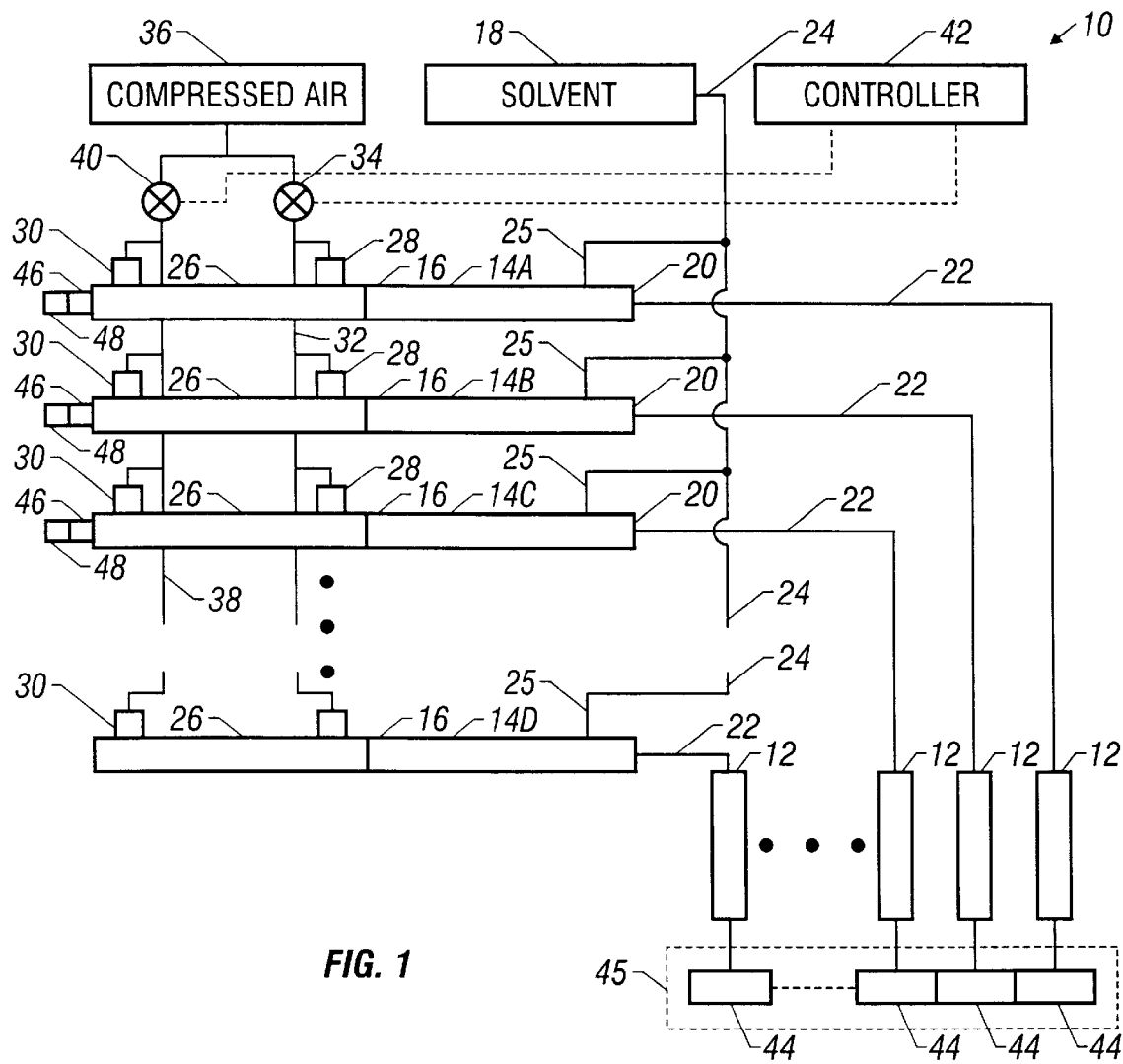
FIG. 1 is a schematic view of a system for supplying solvent to a plurality of chromatography columns.

Referring to FIG. 1, there is shown system 10 for supplying solvent to a plurality of chromatography columns 12.

Figure 2:
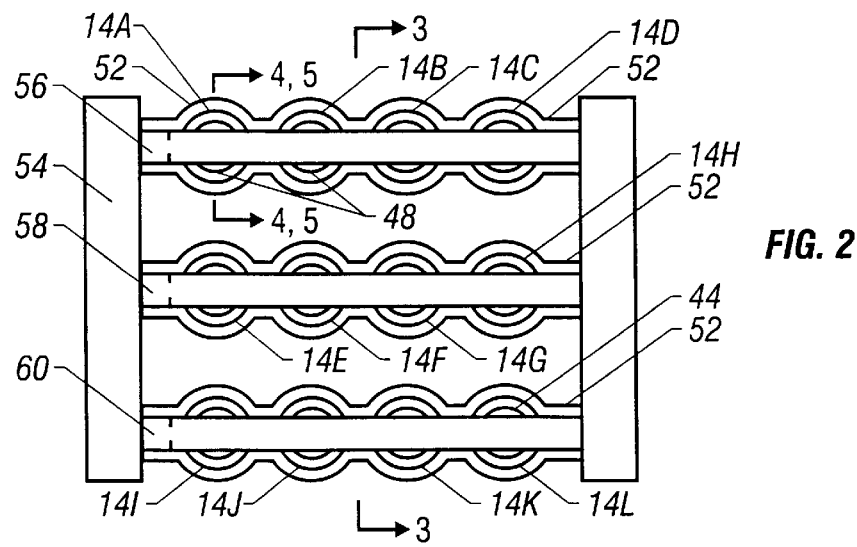
FIG. 2 is an end view of an array of pumps used in the FIG. 1 system.
Figure 3:
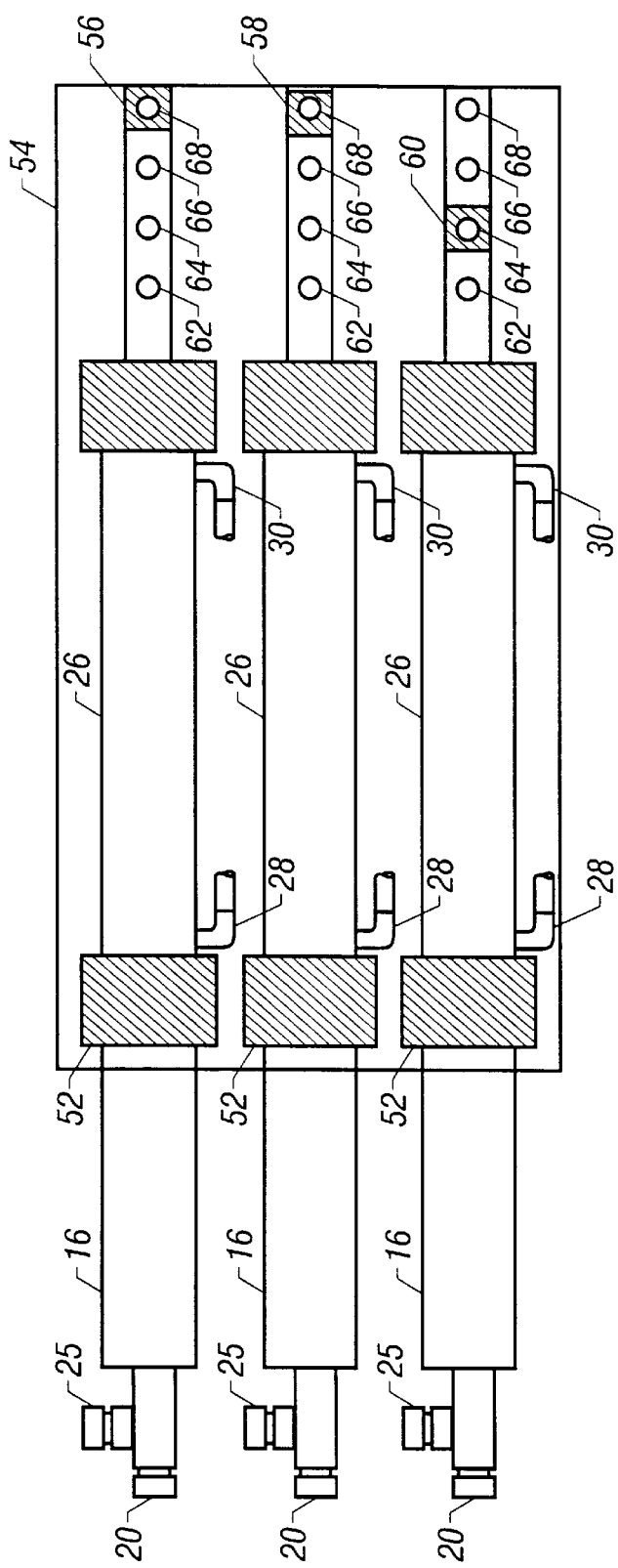
FIG. 3 is a vertical sectional view, taken at 3—3 on FIG. 2, of the FIG. 2 array of pumps (the pumps being in a different orientation than in FIG. 1).

The example of system 10 shown in FIGS. 1, 2 and 3 includes twelve pumps 14A to 14L, though any number of pumps can be used, and rows of pumps can be added in modular fashion. Each pump 14A–L includes a solvent piston chamber portion 16 with an inlet 25 connected to source of solvent 18 and an outlet 20 connected to a respective solvent delivery line 22 to a respective chromatography column 12. The solvent from source 18 is supplied over solvent supply lines 24 to the various pumps 14A–14L.

Each pump 14A–14L also includes a pneumatic cylinder 26 which operates as a piston driver for the respective solvent piston chamber portion 16. Each pneumatic cylinder 26 has pressurized air port 28 connected at the end closest to the solvent piston chamber portion 16 and a pressurized air port 30 connected at the other end of pneumatic cylinder 26. Ports 28 are supplied by supply line 32 connected by solenoid actuated control valve 34 to compressed air source 36. Pressurized air ports 30 are similarly connected by common supply line 38 to compressed air source 36 via solenoid actuated control valve 40. Valves 34 and 40 are controlled by controller 42 to supply compressed air to one set of ports 28 or 30 while permitting the pressurized air to be exhausted from the other set of ports 28 or 30.

Underneath each chromatography column 12 is a respective sample collecting vessel 44 used to collect the sample effluent from the respective column 12. A fraction collecting system 45 is used to collect volumes of effluent from the column associated with successive pump strokes. E.g., vessels 44 can be carried by a moving conveyer belt (not shown) in system 45 so as to advance an empty vessel 44 into position underneath a respective column 12 between strokes of pumps 14A–14L or at other desired intervals. Alternatively, between pump strokes a tube or an arm (not shown) of system 45 can be automatically moved so as to fill different vessels 44. Each pump 14A–14L has an internal drive rod 46 that extends to the left (in the FIG. 1 orientation) as the solvent piston is moved to fill the chamber in solvent piston chamber portion 16 with solvent. Adjustment nuts 48 are on the ends of drive rods 46.

Referring to FIG. 2, it is seen that array 50 of pumps 14A–14L are arranged in three rows of four pumps each. Each row is supported by a horizontal support member 52 to end vertical frame members 54. At the back of the frame members 54 are three horizonal stop bars 56, 58, 60 which set the end of travel positions for adjustment nuts 48, and thus the drive rods 46 for the respective pumps.

Figure 4:
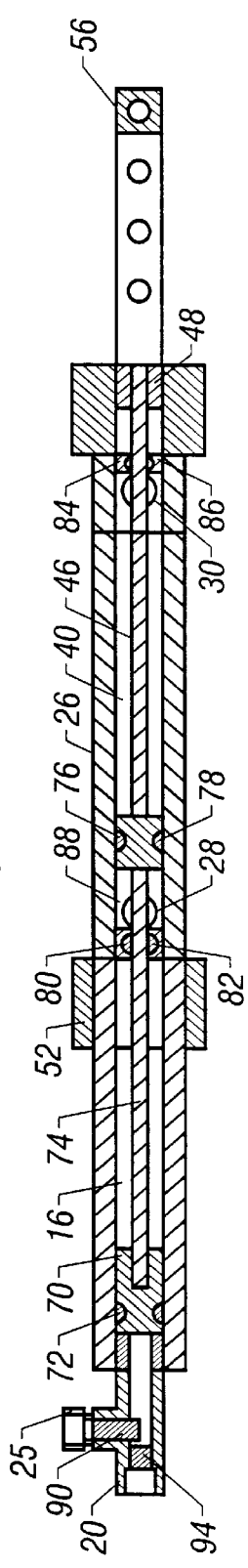
FIG. 4 is a vertical sectional view, taken at 4—4 on FIG. 2, of a pump of the FIG. 2 array shown prior to pulling solvent into the pump with a solvent piston at a zero displacement volume position.
Figure 5:
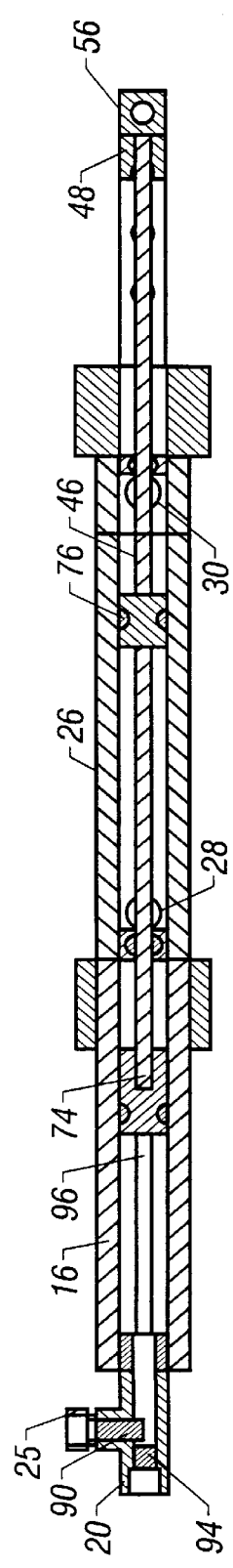
FIG. 5 is a vertical sectional view, taken at 5—5 on FIG. 2, of the FIG. 4 pump showing the solvent piston at a full displacement volume position.

Referring to FIGS. 3, 4, and 5, it is seen that stop bars 56, 58, 60 can be adjustably mounted in different positions by connections to respective holes 62, 64, 66, 68 representing the one-quarter, one-half, three-quarter, and full stroke volume positions. Thus, pumps 14A–14H in the top two rows are set to have full stroke displacement volumes, while pumps 14I–14L in the lowest row are set to deliver a half stroke displacement volumes. The system also includes a pump cessation sensor to sense when all drive rods have ceased motion. E.g., the compressed air source 36 can include a sensor that senses when air stops flowing after valve 34 or 40 has been opened, indicating that all solvent pistons have stopped moving, even if one has been blocked from travel to the end of travel position, e.g., owing to a blocked flow line. Alternatively, sensors on pumps 16 can sense when the drive rods 46 or attached components have ceased motion.

As shown in FIGS. 4 and 5, each solvent piston chamber portion 16 has internal solvent piston 70 with sealing O-rings 72 connected by piston rod 74 to pneumatic cylinder piston 76. O-rings 72 provide a fluid-tight seal for the solvent being pumped. Piston 76 has sealing O-rings 78 to provide an air-tight seal for the pneumatic chambers 88 and 90 on both sides of piston 76. Piston rod 74 passes through sealing member 80 having O-rings 82 to provide a seal for chamber 88. Drive rod 46, connected on the other side of pneumatic piston 76, similarly passes through sealing member 84 and O-rings 86 to provide a seal for chamber 90. Drive rod 46 has a threaded connection on its far end connected to nut 48, which is rotated to adjust the position of piston 70 when nut is stopped at stop bar 56, 58, or 60. In this manner nuts 48 are used to calibrate and provide fine tuning adjustment of the displacement volume of the respective pumps.

In operation, solvent delivery lines 22 are connected to respective pump outlets 20 and to respective columns 12, and collection vessels 44 are set in place. In order to pump displacement volumes of solvent into columns 12, controller 42 provides control signals to valve 34 to supply compressed air from source 36 to ports 28 and to valve 40 to exhaust air from ports 30. The pressurized air is then supplied through ports 28 (to the left hand side of pneumatic piston 76 in the orientation shown in FIGS. 4 and 5), which causes the connected solvent piston 70 to move to the right in FIG. 4 and to achieve the position shown in FIG. 5. In doing so, solvent is supplied through inlet 25 and inflow check valve 90 into pump chamber 96. The pump cessation sensor(s) senses when all solvent pistons 70 have ceased moving (whether at the end of travel position or not) and sends a pump cessation signal to controller 42. Controller 42 then switches valves 34 to the exhaust position, and switches valves 40 to connect compressed air from source 36 to ports 30. The resulting supply of compressed air to the other side of pneumatic piston 76 causes solvent piston 70 to be moved toward the outlet 20 and to displace and discharge the fluid in chamber 96 through check valve 94 to the respective column 12. The displaced volume of solvent passes through the respective chromatography column 12, and the effluent is collected in vessels 44. The pump cessation sensor(s) again senses when all solvent pistons 70 have ceased moving (whether at the end of travel position or not) and sends a pump cessation signal to controller 42. Controller 42 then causes fraction collection system 45 to advance so that a subsequent stroke volume can be delivered by pumps by 14A–14L to new respective vessels 44, and the process is then repeated for the number of stroke volumes desired.

Other embodiments of the invention are within the scope of the claims. E.g., instead of the pneumatic system, a hydraulic system could be used to drive the solvent pistons.

What is claimed is:

1. Apparatus for simultaneously supplying solvent to a plurality of chromatography columns comprising
   a plurality of pumps,
      each said pump having a pump chamber with a movable solvent piston therein and inflow and outflow valves, the outflow valve of each pump being connected to a respective chromatography column,
   a plurality of piston drivers operable to move said solvent pistons in one direction to pull solvent into said respective pump chambers until said pistons achieve respective stop positions corresponding to desired delivery volumes and to move said pistons in the opposite direction to deliver solvent to said respective columns,
   an adjustable stop for each said piston driver to adjustably determine said stop position, and
   a controller for simultaneously causing said piston drivers to simultaneously move said solvent pistons in said one direction and to simultaneously move said solvent pistons in the other direction.

2. The apparatus of claim 1 wherein said controller controls delivery of a common driving force to said piston drivers.

3. The apparatus of claim 2 further comprising a common fluid pressure delivery system that is controlled by said controller and communicates with said piston drivers to provide said common driving force.

4. The apparatus of claim 3 wherein each said piston driver includes a cylinder connected to said fluid pressure delivery system, and wherein pressurized fluid is simultaneously delivered to said cylinders to move said pistons.

5. The apparatus of claim 1 wherein said fluid pressure delivery system is a pneumatic system using a gas.

6. The method of claim 1 wherein said fluid pressure delivery system is a hydraulic system using a liquid.

7. The apparatus of claim 1 wherein said piston drivers have different stop positions.

8. The apparatus of claim 1 wherein said piston drivers have adjustable stop positions.

9. The apparatus of claim 8 wherein said piston drivers have gross stop adjustment mechanisms and fine adjustment mechanisms for said stop positions.

10. The apparatus of claim 1 wherein said pumps are arranged in rows, and rows of pumps are arranged in an array.

11. The apparatus of claim 10 wherein each row has a common stop position provided by a common stop mechanism.

12. The apparatus of claim 1 wherein each pump has a fine adjustment mechanism to adjust its stop position.

13. Apparatus for simultaneously supplying solvent to a plurality of chromatography columns comprising
    a plurality of pumps,
        each said pump having a chamber with a movable solvent piston therein and inflow and outflow valves, the outflow valve of each pump being connected to a respective chromatography column,
    a plurality of piston drivers operable to move said solvent pistons in one direction to pull solvent into said respective chambers until said pistons achieve respective stop positions corresponding to desired delivery volumes and to move said pistons in the opposite direction to deliver solvent to said respective columns,
    a common fluid pressure delivery system connected to said piston drivers, and
    a controller connected to control delivery of pressurized fluid by said common fluid pressure delivery system to said piston drivers for simultaneously causing said piston drivers to move said solvent pistons in said one direction and to simultaneously move said solvent pistons in the other direction.

14. The apparatus of claim 13 wherein each said piston driver includes a cylinder connected to said fluid pressure delivery system, and wherein pressurized fluid is simultaneously delivered to said cylinders to move said pistons.

15. The apparatus of claim 14 wherein each said cylinder has first and second ports, and pressurized fluid is supplied to a first port to move said solvent piston in said one direction, and pressurized fluid is supplied to said second port to move said solvent piston in the opposite direction.

16. The apparatus of claim 14 wherein said fluid pressure delivery system includes a first control valve to supply pressurized fluid to said first ports, and a second control valve to supply pressurized fluid to said second ports.

17. The apparatus of claim 13 wherein said fluid pressure delivery system is a pneumatic system using a gas.

18. The apparatus of claim 13 wherein said fluid pressure delivery system is a hydraulic system using a liquid.

19. The apparatus of claim 13 further comprising a fraction collection system including a plurality of sample collection vessels for collecting samples that have passed through said columns.

20. The apparatus of claim 19 wherein said controller advances said fraction collection system between pump strokes so as to direct the next sample to pass through a said column to a new collection vessel.

21. The apparatus of claim 20 further comprising a pump cessation sensor that senses that said solvent pistons have ceased movement and sends a pump cessation signal to said controller.

22. Apparatus for simultaneously supplying solvent to a plurality of chromatography columns comprising
    a plurality of pumps,
        each said pump having a pump chamber with a movable solvent piston therein and inflow and outflow valves, the outflow valve of each pump being connected to a respective chromatography column,
    a plurality of piston drivers operable to move said solvent pistons in one direction to pull solvent into said respective pump chambers until said pistons achieve respective stop positions corresponding to desired delivery volumes and to move said pistons in the opposite direction to deliver solvent to said respective columns,
    a controller for simultaneously causing said piston drivers to simultaneously move said solvent pistons in said one direction and to simultaneously move said solvent pistons in the other direction,
    a pump cessation sensor that senses that said solvent pistons have ceased movement and sends a pump cessation signal to said controller, and
    a fraction collection system including a plurality of sample collection vessels for collecting samples that have passed through said columns,
    said controller advancing said fraction collection system between pump strokes in response to said pump cessation signal so as to direct the next sample from a said column to be collected in a new collection vessel.

* * * * *